United States Patent [19]

Sato et al.

[11] 4,226,980

[45] Oct. 7, 1980

[54] NOVEL DERIVATIVES OF FORTIMICIN B AND PROCESS FOR PREPARING SAME

[75] Inventors: Moriyuki Sato, Machida; Kenichi Mochida, Hiratsuka; Shigeo Yoshiie, Machida; Yasuki Mori, Kawasaki, all of Japan

[73] Assignee: Abbott Laboratories, North Chicago, Ill.

[21] Appl. No.: 967,352

[22] Filed: Dec. 7, 1978

[51] Int. Cl.[3] .................. A61K 31/71; C07H 15/22
[52] U.S. Cl. .................. 536/17 R; 424/180; 536/4
[58] Field of Search .................. 536/4, 17 R

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,078,138 | 3/1978 | Akita et al. | 536/17 |
| 4,107,435 | 8/1978 | Ross | 536/17 |
| 4,124,756 | 11/1978 | Martin et al. | 536/17 |
| 4,136,254 | 1/1979 | Nagabhushan et al. | 536/17 |

*Primary Examiner*—Johnnie R. Brown
*Attorney, Agent, or Firm*—Fitzpatrick, Cella, Harper & Scinto

[57] ABSTRACT

Semisynthetic antibacterial compounds are produced by chemically modifying the antibacterial compound fortimicin B.

5 Claims, No Drawings

NOVEL DERIVATIVES OF FORTIMICIN B AND PROCESS FOR PREPARING SAME

BACKGROUND OF THE INVENTION

The present invention relates to novel derivatives of fortimicin B, the acid addition salts thereof and a process for preparing the same.

Fortimicins (A, B and C) are compounds belonging to pseudodisaccharide antibiotics containing 1,4-diaminocyclitol. The physical properties and antibacterial activities of these compounds, the processes of producing them by using microorganisms, and processes for separation and purification thereof from culture liquors, etc. are described in detail in U. S. Pat. Nos. 3,931,400, 3,976,768 and 4,048,015.

The planar structural formulae of the fortimicins, are illustrated in said United States Patents and their structural formulae showing absolute coordination are described in the specification of Japanese Published Unexamined Patent Application No. 5014078.

Fortimicins (A, B and C) all have antibacterial activity, but the antibacterial activity of fortimicin B is not as good as the other factors; and fortimicin A and fortimicin C are slightly unstable under strongly alkaline conditions. Therefore, compounds having more distinguished properties are in demand.

As a result of various studies, it has been found that certain 4-N-substituted derivatives of fortimicin B have enhanced antibacterial activity and good stability under alkaline conditions (Japanese Published Unexamined Patent Application No. 50140/78).

Moreover, it has now been found that certain 4,2'-di-N-substituted derivatives of fortimicin B have good stability under strongly alkaline conditions and enhanced antibacterial activity aginst a broad spectrum of pathogenic microorganism including strains resistant to known antibiotics.

SUMMARY OF THE INVENTION

The present invention relates to 4,2'-di-N-substituted derivatives of fortimicin B, represented by the general formula (I):

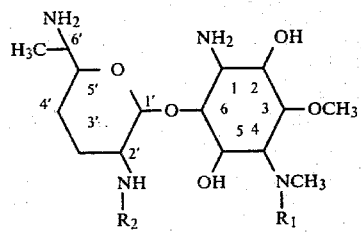

wherein $R_1$ and $R_2$ may be the same or different, and $R_1$ represents a

or $-CH_2-R_3$ group, $R_2$ represents a

or $-CH_2-R_4$ group and wherein $R_3$ and $R_4$ represent an aminoalkyl group having 1 to 8 carbon atoms, a hydroxyalkyl group having 1 to 8 carbon atoms, a carbamoylaminoalkyl group having 2 to 9 carbon atoms or an aminohydroxyalkyl group having 2 to 9 carbon atoms. The invention also pertains to a process for preparing the same.

Included in the composition of matter aspect of the invention are the non-toxic acid addition salts of the compounds of the above general formula.

DETAILED DESCRIPTION

Compounds of the present invention are 4,2'-di-N-substituted derivatives of fortimicin B, represented by the general formula (I):

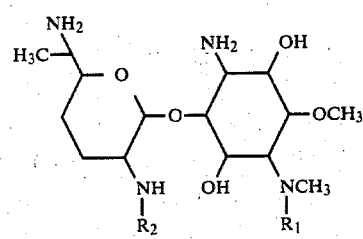

wherein $R_1$ and $R_2$ may be the same or different, and $R_1$ represents a

or $-CH_2-R_3$ group, $R_2$ represents a

or $-CH_2-R_4$ group and wherein $R_3$ and $R_4$ represent an aminoalkyl group having 1 to 8 carbon atoms, a hydroxyalkyl group having 1 to 8 carbon atoms, a carbamoylaminoalkyl group having 2 to 9 carbon atoms and an aminohydroxyalkyl group having 2 to 9 carbon atoms and the acid addition salts thereof.

4,2'-di-N-substituted derivatives of fortimicin B represented by the general formula (I), are exemplified in the following Table 1 together with the values of their physical properties. For reference, the physical properties of fortimicin B, fortimicin A and fortimicin C are also set forth.

The Rf values of the compounds of the invention as well as the starting compounds on thin layer chromatography (TLC) using various solvents and silica gel plates are set forth in Table 2. In the TLC treatment, DC-Fertigplatten Kieselgel 60 F254 (product of E. Merck & Co.) was used as a silica gel plate and in color reaction, ninhydrin or iodine was used. The solvent systems given in Table 2 are as follows:

A: isopropanol—28% aqueous ammonia-chloroform (2:1:1 volume)

B: isopropanol—28% aqueous ammonia-chloroform (4:1:1 by volume)

C: the lower layer of methanol-28% aqueous ammoniachloroform (1:1:1 by volume)

D: chloroform: methanol (90:10 by volume)

E: chloroform:methanol (95:5 by volume)

Furthermore in the following Table 3, the antibacterial activity (MIC) of the compounds are set forth. The measurement was carried out according to the Japanese Antibiotic Medicament Standard using a medium having a pH of 7.2. Numbers of the compounds in Table 3 correspond to those in Tables 1 and 2.

Table 1

| Compound number | $R_1$ in general formula (I) | $R_2$ in general formula (I) | Compound name | Elementary analysis (%) Upper row: Calculated Lower row: Found | $[\alpha]_D$ of sulfate *1:23° C. *2:25° C. |
|---|---|---|---|---|---|
| 1 | H | H | fortimicin B | as $C_{15}H_{32}N_5O_5 \cdot H_2O$<br>C 49.15 H 8.80 N 15.29<br>49.36  8.77  15.38 | *1 (Note 1) +30.3° (c=1.0, water) |
| 2 | $-\underset{\underset{O}{\|\|}}{C}-CH_2-NH_2$ | H | fortimicin A | as $C_{17}H_{35}N_5O_6$<br>C 50.35 H 8.70 N 17.27<br>50.23  8.67  17.49 | *2 (Note 1) +26.0° (c=0.2, water) |
| 3 | $-\underset{\underset{O}{\|\|}}{C}-CH_2-NH-\underset{\underset{O}{\|\|}}{C}-NH_2$ | H | fortimicin C | as $C_{18}H_{36}N_6O_7 \cdot 2H_2O$<br>C 45.00 H 8.33 N 17.50<br>44.84  8.19  17.36 | *2 (Note 1) +84.3° (c=0.1, water) |
| 4 | $-\underset{\underset{O}{\|\|}}{C}-CH_2-NH-\underset{\underset{O}{\|\|}}{C}-NH_2$ | $-\underset{\underset{O}{\|\|}}{C}-CH_2-NH-\underset{\underset{O}{\|\|}}{C}-NH_2$ | 2'-N-hydantoyl fortimicin C | as $C_{21}H_{40}N_8O_9 \cdot H_2SO_4 \cdot C_2H_5OH \cdot H_2O$<br>C 38.86 H 7.09 N 15.77<br>38.76  6.95  16.03 | *1 +58.5° (c=0.2, water) |
| 5 | $-CH_2-CH_2-NH_2$ | $-CH_2-CH_2-NH_2$ | 4,2'-di-N-(2-aminoethyl) fortimicin B | as $C_{19}H_{42}N_6O_5 \cdot 3H_2SO_4 \cdot C_2H_5OH \cdot 2H_2O$<br>C 31.10 H 7.21 N 10.36<br>31.01  7.50  10.40 | *1 +61.0° (c=0.5, water) |
| 6 | $-CH_2-\underset{OH}{CH}-CH_2-\underset{NH_2}{CH_2}$ | $-\underset{\underset{O}{\|\|}}{C}-CH_2-NH_2$ | 4-N-[(S)-4-amino-2-hydroxybutyl]-2'-N-glycyl fortimicin B | as $C_{21}H_{44}N_6O_7 \cdot 2.5H_2SO_4 \cdot C_2H_5OH \cdot H_2O$<br>C 34.45 H 7.17 N 10.48<br>34.29  7.45  10.61 | *1 +70.0° (c=0.2, water) |
| 7 | $-CH_2-\underset{OH}{CH}-CH_2-\underset{NH_2}{CH_2}$ | $-CH_2-CH_2-NH_2$ | 4-N-[(S)-4-amino-2-hydroxybutyl]-2'-N-(2-aminoethyl) fortimicin B | as $C_{21}H_{46}N_6O_6 \cdot 3H_2SO_4 \cdot C_2H_5OH \cdot H_2O$<br>C 33.00 H 7.23 N 9.98<br>32.76  7.18  9.70 | *1 +67.0° (c=0.2, water) |
| 8 | $-CH_2-\underset{OH}{CH}-CH_2-\underset{NH_2}{CH_2}$ | $-\underset{\underset{O}{\|\|}}{C}-\underset{OH}{CH}-CH_2-\underset{NH_2}{CH_2}$ | 4-N-[(S)-4-amino-2-hydroxybutyl]-2'-N-[(S)-4-amino-2-hydroxybutyryl] fortimicin B | as $C_{23}H_{48}N_6O_8 \cdot 2.5H_2SO_4 \cdot C_2H_5OH \cdot 1.5H_2O$<br>C 34.76 H 7.35 N 9.73<br>34.84  7.61  9.78 | *2 +87.5° (c=0.2, water) |
| 9 | $-CH_2-\underset{OH}{CH}-CH_2-\underset{NH_2}{CH_2}$ | $-CH_2-\underset{OH}{CH}-CH_2-\underset{NH_2}{CH_2}$ | 4,2'-di-N-[(S)-4-amino-2-hydroxybutyl]-fortimicin B | as $C_{23}H_{50}N_6O_7 \cdot 3H_2SO_4 \cdot C_2H_5OH \cdot 1.5H_2O$<br>C 33.74 H 7.36 N 9.44<br>33.77  7.61  9.20 | *1 +88.0° (c=0.2, water) |
| 10 | $-CH_2-\underset{OH}{CH}-CH_2-\underset{NH_2}{CH_2}$ | $-CH_2-CH_2OH$ | 4-N-[(S)-4-amino-2-hydroxybutyl]-2'-N-(2-hydroxyethyl) fortimicin B | as $C_{21}H_{45}N_5O_7 \cdot 2.5H_2SO_4 \cdot C_2H_5OH \cdot H_2O$<br>C 35.01 H 7.41 N 8.89<br>34.92  7.56  8.67 | *1 +59.5° (C=0.2, water) |

Note (1) measured in the form of free base

Table 2

| Compound number | Compound name | Solvent system | Rf value | Color reaction |
|---|---|---|---|---|
| 1 | fortimicin B | A | 0.56 | ninhydrin |

Table 2-continued

| Compound number | Compound name | Solvent system | Rf value | Color reaction |
|---|---|---|---|---|
| 2 | fortimicin A | A | 0.47 | " |
| 3 | fortimicin C | A | 0.43 | " |
| 4 | 2'-N-hydantoylfortimicin C | A | 0.31 | iodine |
| 5 | 4,2'-di-N-(2-aminoethyl)fortimicin B | A | 0.35 | " |
| 6 | 4-N-[(S)-4-amino-2-hydroxybutyl]-2'-N-glycylfortimicin B | A | 0.33 | " |
| 7 | 4-N-[(S)-4-amino-2-hydroxybutyl]-2'-N-(2-aminoethyl)fortimicin B | A | 0.30 | " |
| 8 | 4-N-[(S)-4-amino-2-hydroxybutyl]-2'-N-[(S)-4-amino-2-hydroxybutyryl]fortimicin B | A | 0.25 | " |
| 9 | 4,2'-di-N-[(S)-4-amino-2-hydroxybutyl]fortimicin B | A | 0.20 | " |
| 10 | 4-N-[(S)-4-amino-2-hydroxybutyl]-2'-N-(2-hydroxyethyl)fortimicin B | C | 0.50 | " |
| 11 | 2'-N-[(S)-4-benzyloxycarbonylamino-2-hydroxybutyryl]fortimicin B | B | 0.57 | " |
| 12 | 2'-N-(O-benzylglycolyl)fortimicin B | C | 0.33 | " |
| 13 | 1,6'-di-N-benzyloxycarbonyl-2'-N-[(S)-4-benzyloxycarbonylamino-2-hydroxybutyryl]fortimicin B | D | 0.31 | " |
| 14 | 1,6'-di-N-benzyloxycarbonyl-2'-N-(O-benzylglycolyl)fortimicin B | D | 0.41 | " |
| 15 | 2'-N-glycylfortimicin B | A | 0.45 | " |
| 16 | 2'-N-hydantoylfortimicin B | A | 0.44 | " |
| 17 | 1,6'-N-benzyloxycarbonyl-2'-N-(N-benzyloxycarbonylglycyl)fortimicin B | D | 0.43 | " |
| 18 | 1,6'-di-N-benzyloxycarbonyl-2'-N-hydantoylfortimicin B | B | 0.64 | " |
| 19 | 1,6'-di-N-benzyloxycarbonyl-4,2'-di-N-(N-benzyloxycarbonylglycyl)fortimicin B | D | 0.83 | " |
| 20 | 1,6'-di-N-benzyloxycarbonyl-4-N-[(S)-4-benzyloxycarbonylamino-2-hydroxy butyryl]-2'-N-(N-benzyloxycarbonylglycyl)fortimicin B | D | 0.77 | " |
| 21 | 1,6'-di-N-benzyloxycarbonyl-4,2'-di-N-[(S)-4-benzyloxcarbonyl-amino-2-hydroxybutyryl]fortimicin B | D | 0.53 | " |
| 22 | 1,6'-di-N-benzyloxycarbonyl-4-N-[(S)-4-benzyloxycarbonylamino-2-hydroxybutyryl]-2'-N-(O-benzylglycolyl)fortimicin B | E | 0.79 | " |
| 23 | 2'-N-glycylfortimicin A | A | 0.42 | " |
| 24 | 4-N-[(S)-4-amino-2-hydroxybutyryl]-2'-N-glycylfortimicin B | A | 0.28 | " |
| 25 | 4,2'-di-N-[(S)-4-amino-2-hydroxybutyryl]fortimicin B | A | 0.13 | " |
| 26 | 4-N-[(S)-4-amino-2-hydroxybutyryl]-2'-N-glycolylfortimicin B | C | 0.32 | " |
| 27 | 1,6'-di-N-benzyloxycarbonyl-4-N-[(S)-4-benzyloxycarbonylamino-2-hydroxybutyl]-2'-N-(N-benzyloxycarbonylglycyl)fortimicin B | D | 0.51 | " |
| 28 | 1,6'-di-N-benzyloxycarbonyl-4-N-[(S)-4-benzyloxycarbonylamino-2-hydroxybutyl]-2'-N-(2-benzyloxycarbonylaminoethyl)fortimicin B | D | 0.15 | " |

Table 3

| Microorganism | 1 | 2 | 3 | 5 | 6 | 7 | 8 | 9 | 10 | KA* |
|---|---|---|---|---|---|---|---|---|---|---|
| *Staphylococcus aureus* 209-p | >100 | 0.78 | 6.25 | 1.56 | 1.56 | 0.78 | 0.78 | 0.78 | 1.56 | 0.4 |
| *Staphylococcus aureus* Smith | 100 | 1.56 | 12.5 | 1.56 | 0.78 | 1.56 | 0.78 | 0.78 | 0.78 | 0.4 |
| *Bacillus subtilis* ATCC 6633 | 25 | 0.78 | 3.12 | 1.56 | 0.78 | 0.4 | 0.78 | 0.4 | 0.78 | 0.4 |
| *Escherichia coli* NIHJ-2 | >100 | 1.56 | 3.12 | 3.12 | 3.12 | 3.12 | 1.56 | 1.56 | 6.25 | 1.56 |
| *Escherichia coli* 3100 | 100 | 6.25 | 12.5 | 6.25 | 6.25 | 3.12 | 3.12 | 3.12 | 3.12 | 3.12 |
| *Klebsiella pneumoniae* #8045 | 100 | 1.56 | 12.5 | 3.12 | 1.56 | 0.78 | 1.56 | 1.56 | 6.25 | 0.78 |
| *Shigella sonnei* ATCC 9290 | >100 | 6.25 | 25 | 12.5 | 6.25 | 3.12 | 6.25 | 3.12 | 6.25 | 3.12 |
| *Providencia* sp. KY3950 | >100 | 12.5 | 25 | 12.5 | 6.25 | 6.25 | 6.25 | 1.56 | 12.5 | 12.5 |
| *Pseudomonas aeruginosa* BMH#10 | >100 | 0.78 | 3.12 | 1.56 | 0.78 | 0.78 | 0.78 | 0.78 | 1.56 | 25 |
| *Escherichia coli* $R_{17}Z$-343[1]** | >100 | 1.56 | 3.12 | 3.12 | 1.56 | 0.78 | 0.78 | 1.56 | 3.12 | 12.5 |
| *Escherichia coli* $R_{18}$KY-83212** | >100 | 3.12 | 12.5 | 6.25 | 3.12 | 3.12 | 6.25 | 1.56 | 1.56 | >100 |
| *Escherichia coli* $R_{19}$KY-8348[3]** | >100 | >100 | >100 | 25 | 3.12 | 0.78 | 3.12 | 6.25 | 100 | >100 |
| *Escherichia coli* 57R/W677[4]** | >100 | 6.25 | 6.25 | 6.25 | 6.25 | 3.12 | 3.12 | 3.12 | 100 | 100 |
| *Pseudomonas aeruginosa* $R_4$KY8511[3]** | >100 | >100 | >100 | 100 | 50 | 12.5 | 100 | 100 | >100 | >100 |
| *Pseudomonas aeruginosa* $R_9$KY8516[1]** | >100 | 12.5 | 50 | >100 | 25 | 6.25 | 50 | 3.12 | 50 | >100 |
| *Providencia* sp. 164[5]** | >100 | 3.12 | 25 | 50 | 6.25 | 12.5 | 6.25 | 3.12 | 50 | >100 |
| *Klebsiella pneumniae* 3020 Y60[4]** | >100 | 6.25 | 50 | 25 | 6.25 | 6.25 | 12.5 | 3.12 | 100 | >100 |

*KA: kanamycin A
**[1] producing kanamycin acetyltransferase
[2] producing gentamicin nucleotidyltransferase and neomycin phosphotransferase II
[3] producing gentamicin acetyltransferase I
[4] producing gentamicin nucleotidyltransferase
[5] producing gentamicin acetyltransferase II
Bacteria inactivates antibiotics by the enzymes mentioned above.

As is evident from the foregoing Table 3, the compounds of the present invention exhibit good antibacterial activity against various microorganisms including resistant strains and are, therefore, useful as antibacterial agents or antiseptics.

The non-toxic acid addition salts of the present compounds also exhibit a broad antibacterial spectrum and are likewise useful as antibacterial agents. The non-toxic acid addition salts include the mono-, di-, tri-, tetra-, penta- and hexa-salts obtained by reacting one molecule of the compound represented by said general formula (I) with one to six equivalents of a pharmaceutically acceptable, non-toxic acid. Suitable acids include inorganic acids such as sulfuric acid, hydrochloric acid, hydrobromic acid, hydroiodic acid, phosphoric acid, carbonic acid, nitric acid, etc., organic acids such as acetic acid, fumaric acid, malic acid, citric acid, mandelic acid, succinic acid, ascorbic acid, etc., and amino acids such as aspartic acid and the like.

Generally speaking, the present compounds are synthesized according to the processes in the following Flow Sheet I.

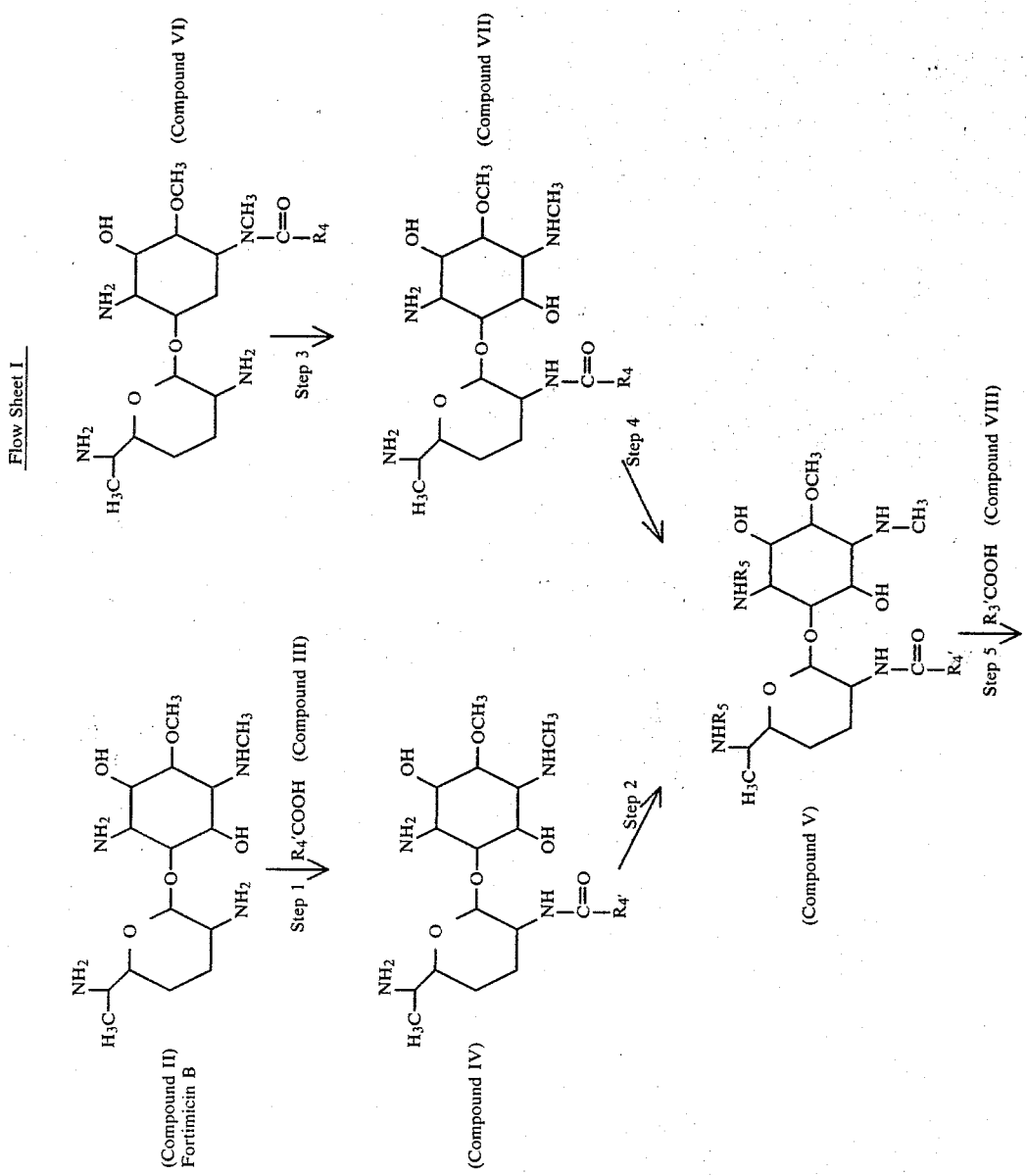
Flow Sheet I

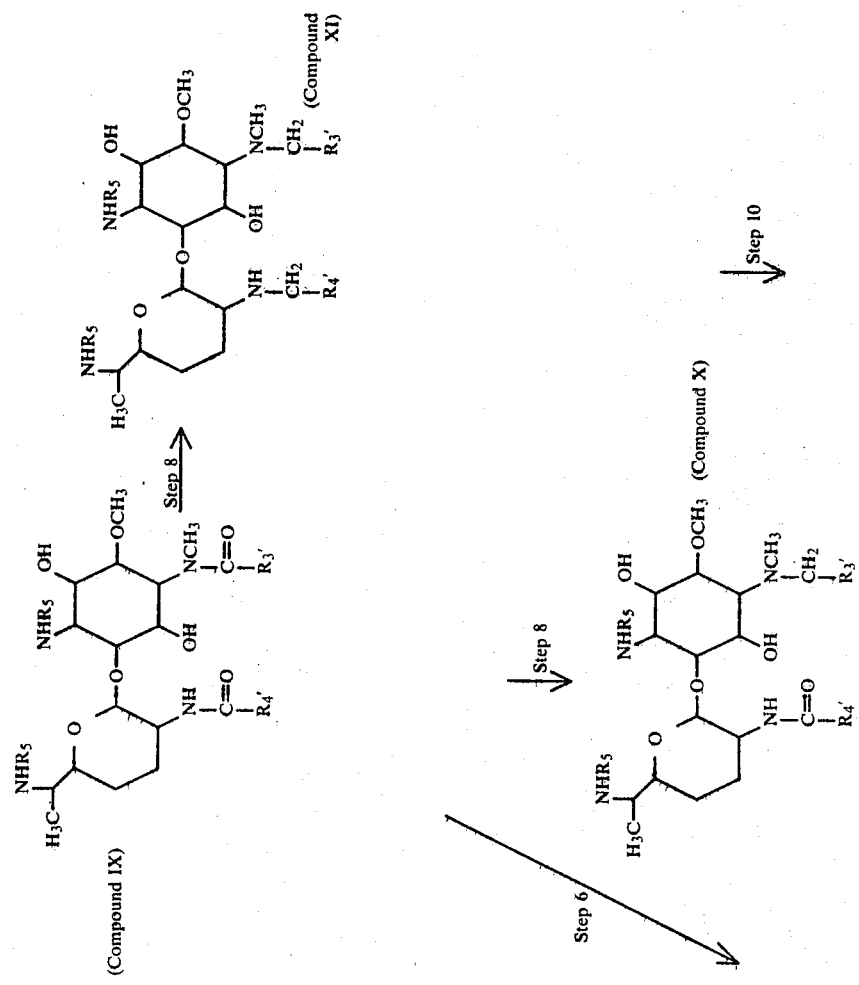

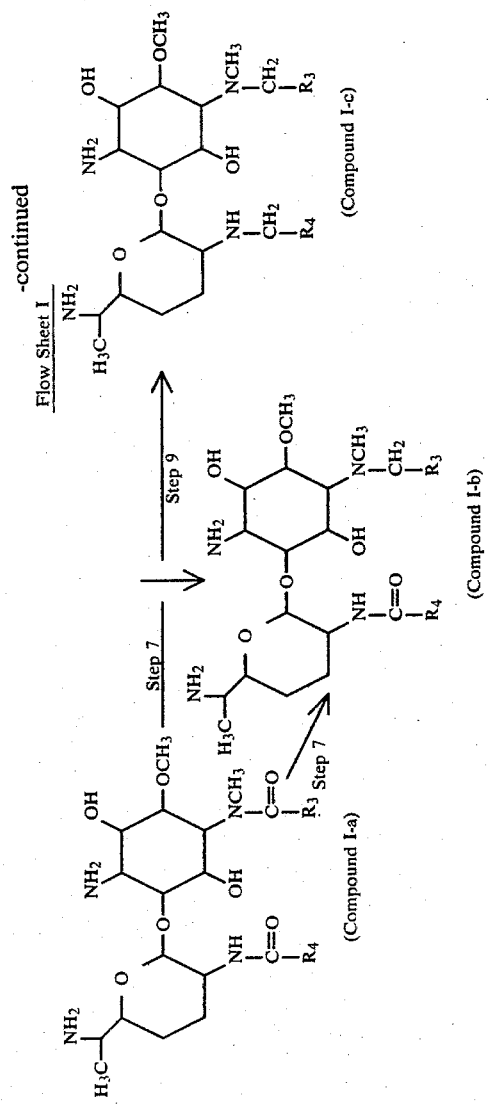

More particularly, when the desired compound is Compound I-a represented by the general formula (I) wherein $R_1$ is

and $R_2$ is

the Compound is synthesized by Step 1→Step 2→Step 5→Step 6, or by Step 3→Step 4→Step 5→Step 6.

When the desired compound is Compound I-b represented by the general formula (I) wherein $R_1$ is —$CH_2$—$R_3$ and $R_2$ is

and Compound I-c represented by the general formula (I) wherein $R_1$ is —$CH_2R_3$ and $R_2$ is —$CH_2$—$R_4$, the compound is synthesized by Step 7 using Compound I-a as the starting material, or by Step 8→Step 9 or Step 8→Step 10 using a precursor (Compound IX) of Compound I-a as the starting material.

Among the compounds represented by the general formula (I) thus obtained, Compound I-a is slightly unstable under strongly alkaline conditions as is fortimicin A and fortimicin C. That is, Compound I-a is almost decomposed in an alkaline solution with a pH of 10 at room temperature for 2 weeks to form compounds having low activity. Compound I-b, on the other hand, is more stable than Compound I-a, and is barely decomposed in an alkaline solution with a pH of 10 at room temperature for 2 weeks. Compound I-c is even more stable, and is not decomposed on heating at a temperature of 100° C. for several hours in an alkaline solution saturated with barium hydroxide.

The individual steps of the foregoing process are as follows.

Step 1

Preparation of Compound IV from fortimicin B (Compound II):

Fortimicin B is acylated in a suitable solvent by using an acylating agent to form Compound IV in which the amino group at the 2'-position of fortimicin B is a acylated.

As an acylating agent, derivatives of a carboxylic acid represented by the general formula (III) $R_4'$COOH [wherein $R_4'$ is a carbamoylaminoalkyl group, substituted aminoalkyl group (the substituent represents an amino-protecting group), hydroxyalkyl group or substituted aminohydroxyalkyl group (the substituent represents an amino-protecting group), where said aminoprotecting group may be the same as or different from the aminoprotecting group $R_5$ of Compound V obtained in Step 2 or Step 4 mentioned below]. For example, acid anhydrides of carboxylic acids represented by the general formula (III), active esters of said carboxylic acids with a compound selected from a group of

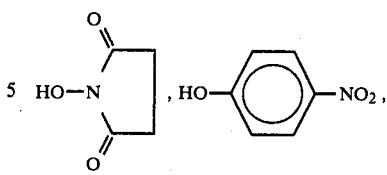

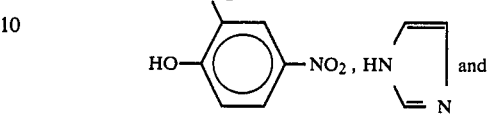

or acid hydrides of
said carboxylic acids may be used.

Fortimicin B is used in a concentration of 1 to 250 mM, preferably 10 to 100 mM. Acylating agents are used in a concentration of 0.5 to 2 moles, preferably 1 to 1.5 moles per mole of fortimicin B.

As the solvent, dimethylformamide, dimethylacetamide, tetrahydrofuran, dioxane, 1,2-dimethoxyethane, methanol, ethanol, water and a mixture thereof are used.

Reaction is carried out at a temperature of 0° C. to room temperature for 15 minutes to 20 hours.

The reaction mixture containing Compound IV prepared by the foregoing process can be utilized as it is or, after isolation, in the successive step to prepare Compound V.

Purification and isolation of Compound IV from the reaction mixture can be carried out in the following manner. The solvent is distilled off from the reaction mixture to obtain a residue. The residue is subjected to partition between an organic solvent such as chloroform and water. The water layer obtained is subjected to column chromatography using an ion exchange resin such as Amberlite CG-50 (product of Rohm & Haas Co.) to adsorb the desired compound thereon. Then, elution is carried out with a suitable solvent. Fractions containing Compound IV are combined and the solvent is distilled off to obtain Compound IV.

Step 2

Preparation of Compound V from Compound IV:

Compound IV and an amino-protecting reagent are reacted in a suitable solvent to obtain Compound V in which the amino groups at the 1- and 6'-positions of Compound IV are protected with an amino-protecting group $R_5$.

As an amino-protecting reagent, those generally used in peptide-synthesis may be used. Examples of preferable aminoprotecting reagents are:

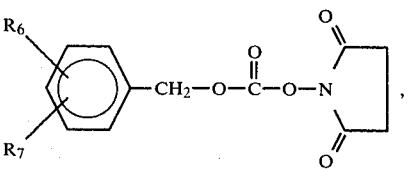

-continued

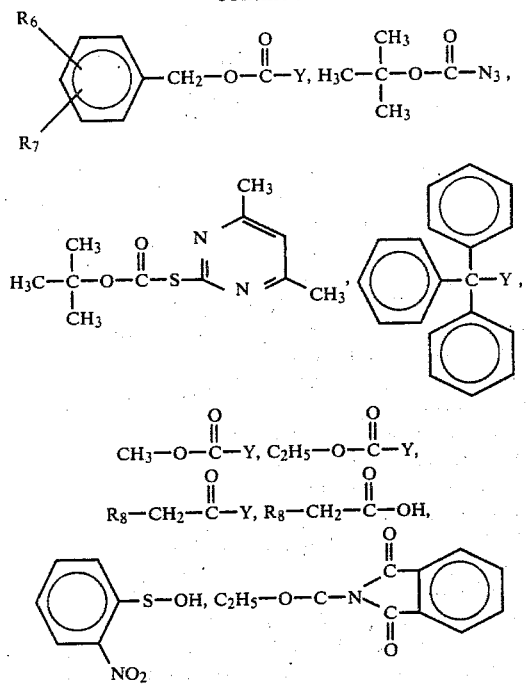

[wherein $R_6$ and $R_7$ may be the same or different and are H, OH, $NO_2$, Cl, Br, I, an alkyl group having 1 to 5 carbon atoms or an alkoxy group having 1 to 5 carbon atoms, $R_8$ is H, F, Cl, Br, I or an alkyl group having 1 to 5 carbon atoms and Y is Cl, Br or I].

As the solvent, dimethylformamide, dimethylacetamide, tetrahydrofuran, dioxane, 1,2-dimethoxyethane, methanol, ethanol, acetone, water and a mixture thereof are used in the reaction. Among these solvents, methanol is more preferable.

Compound IV is used in a concentration of 1 to 250 mM, preferably 10 to 100 mM. The amount of aminoprotecting reagent utilized in the reaction is appropriately 1 to 4 moles, more preferably 2 to 2.5 moles per mole of Compound IV.

Reaction is carried out at a temperature of 0° to 60° C., preferably 0° C. to room temperature for 2 to 18 hours.

The reaction mixture containing Compound V prepared by the foregoing process can be utilized as it is or after isolation in the successive step. To isolate and purify Compound V from the reaction mixture, the solvent is distilled off from the reaction mixture to obtain a residue. An organic solvent such as chloroform or ethyl acetate is added to the residue to extract the soluble portions. The extract is subjected to column chromatography using silica gel such as Kieselgel 60 (product of E. Merck & Co.). In this case, elution is carried out with an organic solvent such as chloroformmethanol or ethylacetate-ethanol and fractions showing a specific Rf value are collected and concentrated to dryness, whereby a white powder of the desired compound is obtained.

Compound V thus obtained can be utilized as a starting material for preparing Compound I-a, Compound I-b and Compound I-c.

In the preparation of Compound I-a or Compound I-b from Compound V, since Compound I-a and Compound I-b are less stable than Compound I-c in strongly alkaline conditions, it is desirable to use Compound V as a starting material which has amino protecting groups eliminable under conditions other than an alkaline condition.

Examples of the amino-protecting reagents of such Compound V are:

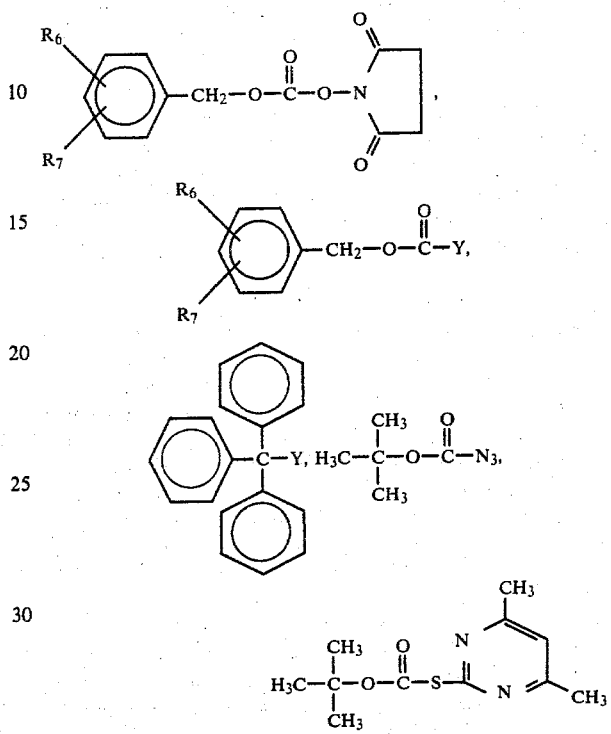

(wherein $R_6$, $R_7$ and Y have the same significance as defined above).

Compound I-c is stable in both acidic and alkaline conditions, and when Compound V is utilized as a starting material for preparing Compound I-c, any aminoprotecting reagent can be utilized.

Step 3

Preparation of Compound VII: from Compound VI

A 4-N-acylfortimicin B derivative (Compound VI) such as fortimicin A or fortimicin C (the process of preparing the derivative is described in Japanese Published Unexamined Patent Application No. 50140/78) is maintained in an alkaline condition in a suitable solvent to form 2'-N-acylfortimicin derivative (Compound VII) wherein the acyl group at the 4-position of 4-N-acylfortimicin derivative rearranges to the 2'-position.

As the solvent, water, methanol, ethanol, dimethylformamide, dimethylacetamide tetrahydrofuran, dioxane, 1,2-dimethoxyethane and a mixture thereof are used. When the solvent includes water, the reaction is carried out at a pH of 7 to 12, preferably 8 to 11, and at a temperature of from room temperature to 100° C. for one hour to 2 weeks. Compound VI is used in a concentration of 1 to 250 mM, preferably 10 to 100 mM.

The reaction mixture containing Compound VII thus produced can be utilized as it is or, after isolation, as a starting material for preparing Compound V.

To isolate and purify Compound VII from the reaction mixture, the reaction solution, as it is or after dilution with water, is charged into a column packed with an ion-exchange resin such as Amberlite CG-50, to adsorb the desired compound thereon. Then, elution is carried out with a suitable solvent. Fractions containing Compound VIII are combined and the solvent is distilled off to obtain Compound VII.

Step 4

Preparation of Compound V from Compound VII:

Compound VII and an amino-protecting reagent are reacted in suitable solvent to obtain Compound V wherein the amino groups at the 1- 6'-positions of Compound VII are protected with amino-protecting groups and, when R₄ has an amino group, such group is also protected.

The amino-protecting reagents and solvents are selected from those as used in Step 2 and the reaction temperature and reaction time are also similar to those in Step 2.

Compound VII is used in a concentration of 1 to 250 mM, preferably 10 to 100 mM. The amount of amino-protecting reagents used in the reaction is 2 to 5 moles per mole of Compound VII. When Compound VII has an R₄ group not having any amino group or an R₄ group wherein an amino group is already protected, the amount of amino-protecting reagent is preferably 2 to 2.5 moles per moles of Compound VII. When Compound VII has an R₄ group having free amino groups, 1 to 1.5 moles of amino-protecting reagent per one amino group are additionally added.

Step 5

Preparation of Compound IX from Compound V:

Compound v is acylated using an acylating reagent in a suitable solvent to obtain Compound IX wherein the amino-group at the 4-position of Compound V is acylated.

As an acylating reagent, derivatives of carboxylic acids represented by the general formula (VIII); R₃'COOH, wherein R₃' represents a carbamoylaminoalkyl group, hydroxyalkyl group, substituted aminoalkyl group (the substituent represents an aminoprotecting group), or substituted aminohydroxyalkyl group (the substituent represents an aminoprotecting group) may be used. The amino-protecting groups may be the same as or different from the aminoprotecting group R₅ in Compound V. For example, acid anhydrides of carboxylic acids represented by the general formula (VIII), active esters of said carboxylic acids with a compound selected from the group consisting of:

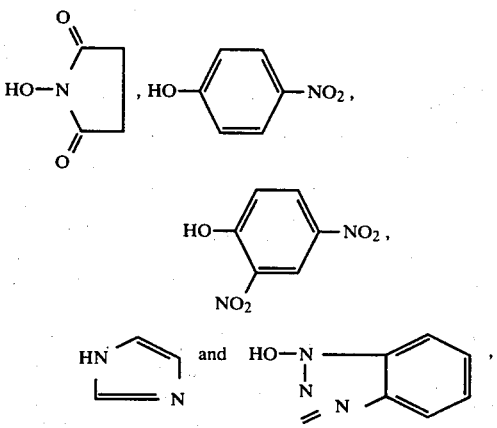

acid hydrides of said carboxylic acids are appropriate.

Compound V is used in a concentration of 1 to 250 mM, preferably 10 to 100 mM, and the acylating reagents are used in a concentration of 1 to 1.5 moles per mole of Compound V.

As the solvent, dimethylformamide, dimethylacetamide, tetrahydrofuran, dioxane, 1,2-dimethoxyethane, methanol, ethanol, water, and a mixture thereof are used. Tetrahydrofuran is preferred.

The reaction is carried out at a temperature of 0° C. to 70° C., preferably 0° C. to room temperature, for 15 minutes to 20 hours, preferably 1 to 18 hours.

In addition to this procedure, the DCC method can also be used for the acylation.

Compund IX, formed in the reaction solution according to the above procedure, or the reaction mixture containing Compound IX can be used for preparing Compounds I-a, X and XI.

To isolate and purify Compound IX from the reaction solution, the solvent is distilled off from the reaction solution to obtain a residue. The residue is mixed with an organic solvent such as chloroform, ethylacetate, or the like to dissolve extractable substances. Then, the resulting extract is subjected to column chromatography packed with silica gel such as Kieselgel 60 (E. Merck & Co.). Elution is carried out with an organic solvent such as chloroform-methanol, or ethylacetate-ethanol, and fractions containing Compound IX are combined and the solvent is removed therefrom to obtain Compound IX.

Step 6

Preparation of Compound 1-a from Compound IX:

The amino-protecting groups R₅ of Compound IX obtained in Step 5 as well as the amino-protecting groups in R₃' and R₄', if such are present, are removed by a method known per se to obtain Compound I-a.

For example, when the protecting group is a benzyloxycarbonyl group, the protecting group can be removed by catalytic hydrogenolysis in the presence of a metal catalyst such as palladium-carbon, platinum, rhodium, etc., and in the presence of an acid such as hydrochloric acid, hydrobromic acid, acetic acid, etc. in a solvent such as water, tetrahydrofuran, dimethylacetamide, dimethylformamide, lower alcohols, dioxane, ethyleneglycoldimethylether, or combinations thereof, etc., preferably in methanol at room temperature and atmospheric pressure, while passing hydrogen gas through the reaction mixture.

Usually 1 to 10% by weight of the metal catalyst is used on the basis of Compound IX, and the concentration of Compound IX is usually 1 to 200 mM, preferably about 50 mM.

The acid is added to the reaction mixture so that pH is maintained at 4 or less. The end of the reaction can be confirmed by the completion of generation of carbon dioxide, thin layer chromatography, and the like.

When the protecting group is a tertiary butoxycarbonyl group, its removal can be carried out in the presence of hydrochloric acid or trifluoroacetic acid in a non-aqueous solvent such as dichloromethane, chloroform, trichloroethylene or ethylacetate.

Compound IX is used in a concentration of 1 to 200 mM, preferably about 50 mM.

In such manner, the desired product is formed in the reaction mixture. It can then be separated and purified by known methods using ion-exchange resins, silica gel chromatography, or the like. For example, according to a method using an ion-exchange resin, the reaction mixture, after filtration, if necessary, is evaporated to dryness. The resulting residue is dissolved in water and the pH is adjusted to about 6 by addition of an alkali, such as sodium hydroxide. Thereafter, the resulting solution is charged into a column packed with, for example, Amberlite CG-50 to adsorb the desired product. Then, the elution is carried out with a suitable solvent and the eluate is taken in fractions. Fractions having activity are combined and the solvent is distilled off to obtain the desired product.

Compound I-a after isolation, or the residue containing compound I-a obtained by evaporation of the reaction solution, can be used to produce Compound I-b and Compound I-c.

Step 7

Preparation of Compound I-b and Compound I-c from Compound I-a:

Compound I-a obtained in Step 6 is reduced in an appropriate solvent in the presence of a reducing agent for converting the carbonyl group in the amide to a methylene group at a temperature of room temperature to reflux temperature of the solvent to obtain Compound I-b and Compound I-c.

As the solvent, tetrahydrofuran, dioxane, diethylether, etc. are appropriate. As the reducing agent, an excess amount, usually 10-fold or more of lithium aluminum hydride, diborane, etc. to Compound I-a is used.

In this step, when the reaction is carried out at a higher temperature and for a longer period. Compound I-c is mainly obtained and when at a lower temperature and for a shorter period, a mixture of Comound I-b and Compound I-c is obtained.

Purification of the desired product is carried out, for example, with an ion-exchange resin. After the excess reducing agent in the reaction mixture is decomposed with ethylacetate, water, or the like, most of the solvent is distilled off under reduced pressure. The resulting residue, in a semi-solid state, is admixed with water to extract water-soluble components, and the resulting extract is subjected to column chromatography using a weakly acidic ion-exchange resin. such as Amberlite CG-50. The column is washed with water and then elution is carried out with aqueous ammonia. Fractions containing Compound I-b or Compoound I-c are collected, and aqueous ammonia is removed by distillation to obtain Compound I-b or Compound I-c as a white powder. Alternatively, separation and purification of the desired product can be carried out according to known methods such as silica gel chromatography, or the like.

Step 8

Preparation of Compound X and Compound XI from Compound IX:

Compound IX obtained in Step 5 is reduced in a suitable non-aqueous solvent in the presence of a reducing agent for converting the carbonyl group in the amide group to a methylene group at a temperature of from room temperature to reflux temperature of the solvent to obtain Compound X and Compound XI.

As the solvent, tetrahydrofuran, dioxane, diethylether, or a mixture thereof is used. As the reducing agent, diborane, lithium aluminum hydride, etc. are used. For the reaction, Compound IX is used in a concentration of from 1 to 250 mM, preferably 10 to 100 mM and usually 10-fold or more equivalents of the reducing agent to Compound IX is used. The reaction is generally completed in 5 minutes to 18 hours.

When the amino-protecting group of Compound IX used in this step is a benzyloxycarbonyl group and t-butoxycarbonyl group, it is preferably to use diborane as a reducing agent because the carbonyl group in the amide group is converted to the methylene group without impairing the benzyloxycarbonyl group and t-butoxycarbonyl group of Compound IX. Thus Compound X and Compound XI can be obtained in a good yield. [W. V. Curran and R. B. Angier: J. Org. Chem., 31, 3867 (1966)].

When the reaction is carried out at a higher temperature and for a longer period, Compound XI is principally obtained and when at a lower temperature and for a shorter period, Compound X is principally obtained.

Thus Compound X and Compound XI are formed in the reaction solution which can then be used as a starting material for the following Steps 9 and 10 without isolating.

If isolation is desired, the solvent is distilled off from the reaction solution, and then the resulting residue is admixed with water to decompose the remaining hydride. Then, the solvent in the reaction mixture is distilled off and the resulting residue is admixed with an organic solvent such as ethylacetate, chloroform, etc. to extract soluble components. The water layer is divided out and the remaining organic solvent layer is washed with water and dried with a drying agent such as anhydrous sodium sulfate. The solvent is distilled off and the resulting residue is dissolved in an organic solvent such as chloroform. The resulting solution is subjected to silica gel column chromatography to obtain the desired product.

Step 9

Preparation of Compound I-b from Compound X:

The amino-protecting groups of Compound X obtained in Step 8, that is $R_5$ and amino-protecting groups of $R_3'$ or $R_4'$ in Compound X, if such are present, are removed according to the method described in Step 6 wherein Compound X is used in place of Compound IX to obtain Compound I-b.

Step 10

Preparation of Compound I-c from Compound XI:

Compound I-c can be obtained by performing the procedure of Step 9 except that Compound XI is used in place of Compound X.

When Compound X and Compound XI obtained in Step 8 are not separated from each other, the mixture of Compound X and Compound XI is used in place of Compound X of Step 9 to obtain a mixture of Compound I-b and Compound I-c. Compound I-b and Compound I-c can be separated by known methods such as column chromatography using an ion-exchange resin, for example, Amberlite CG-50, etc., silica gel, etc.

The acid addition salts of Compound I obtained as mentioned above, may be produced in a known manner.

For example, Compound I is dissolved in water and an acid is added thereto. Then, a solvent decreasing solubility of acid addition salts of Compound I such as ethanol, etc. is added to the resulting solution to form a precipitate. The precipitate is filtered and dried to obtain the acid addition salt of Compound I as a white to gray powder.

Certain specific embodiments of the invention are illustrated by the following representative examples. In these examples, Examples 1 to 2 illustrate embodiments for carrying out Step 1, Examples 3 to 4 for Step 2, Examples 5 to 6 for Step 3, Examples 7 to 8 for Step 4, Examples 9 to 13 for Step 5, Examples 14 to 18 for Step 6, Examples 19 to 22 for Step 7, Example 23 for Step 8, Example 24 for Step 9 and Example 25 for Step 10. The Rf values set forth in the examples are the results when the compounds are developed on a silica gel plate (DC-Fertigplatten Kieselgel 60 F254 made by E. Merck & Co.) using the following solvent systems.

A: isopropanol-28% aqueous ammonia-chloroform (2:1:1 by volume)
B: isopropanol-28% aqueous ammonia-chloroform (4:1:1 by volume)
C: the lower layer of methanol-28% aqueous ammonia-chloroform (1:1:1 by volume)
D: chloroform-methanol (90:10 by volume)
E: chloroform-methanol (95:5 by volume)

EXAMPLE 1

Preparation of 2'-N-[(S)-4-benzyloxycarbonylamino-2-hydroxybutyryl]fortimicin B (Compound No. 11):

In this example, 8.71 g (25.0 millimoles) of fortimicin B is dissolved in 500 ml of methanol and the solution is stirred under ice cooling (3° to 5° C.). A solution wherein 13.1 g (37.5 millimoles) of N-hydroxysuccinimide ester of (S)-4-benzyloxycarbonylamino-2-hydroxybutyric acid is dissolved in 100 ml of tetrahydrofuran is added dropwise to the above solution over a period of 1.5 hours. After the completion of this addition, the reaction solution is stirred under ice cooling for one hour and at room temperture for 18 hours, and then the solvent is distilled off. The resulting residue is dissolved in 200 ml of water and 100 ml of chloroform and stirred well. The water layer and chloroform layer are divided and the chloroform layer is washed with 50 ml of water. The water layer and the washed water are combined and passed through a column packed with 400 ml of Amberlite CG-50 ($NH_4^+$form). After the column is washed with 2 L. of water, elution is carried out with 0.1N aqueous ammonia and the eluate is taken in 20 ml fractons. Fraction Nos. 68 to 84 containing a compound having an Rf value of 0.57 in solvent system B are combined. The solvent is distilled off to obtain 5.90 g of a white solid.

PMR (methanol-$d_4$) spectra of the product is as follows:

$\delta$1.09 (3H, d), 1.2–1.9 (6H, m), 2.40 (3H, s),
5.04 (2H, s), 7.33 (2H, s)

On the basis of the data, it is confirmed that the product is 2'-N-[(S)-4-benzyloxycarbonylamino-2-hydroxybutyryl]-fortimicin B.

Yield 41%.

EXAMPLE 2

Preparation of 2'-N-(O-benzylglycolyl)fortimicin B (Compound No. 12):

In this example, 2.67 g (16.1 millimoles) of O-benzylglycolic acid and 1.85 g (16.1 millimoles) of N-hydroxysuccinimide are dissolved in 100 ml of tetrahydrofuran and the solution is stirred under ice cooling (3° to 5° C.). Then, 3.33 g (16.1 millimoles) of N,N'-dicyclohexylcarbodiimide is added and the resulting solution is stirred under ice cooling for 2 hours. The thus prepared solution of N-hydroxysuccinimide ester of O-benzylglycolic acid is added to a solution of 4.00 g (11.5 millimoles) of fortimicin B in 100 ml of methanol and stirred at room temperature for 18 hours. The solvent in the reaction solution is distilled off to obtain a solid residue. To the residue 100 ml of ethylacetate and 100 ml of water are added and then the mixture is well stirred. Insoluble matters in the reaction mixture are filtered off and the ethylacetate layer of the filtrate is divided and washed with 50 ml of water. The water layer of the filtrate and the washed water are combined and passed through a column packed with 150 ml of Amberlite CG-50 ($NH_4^+$form). After the column is washed with 700 ml of water, elution is carried out with 0.075N aqueous ammonia. The eluate is taken in 20 ml fractions. Fraction Nos. 26 to 47 containing a compound having an Rf value of 0.33 in solvent system C are combined and the solvent is distilled off to obtain 1.30 g of a white solid. PMR (methanol-$d_4$) spectra of the product is as follows:

$\delta$1.05 (3H, d), 1.2–1.9 (4H, m), 2.40 (3H, s),
3,49 (3H, s), 3.92 (2H, s), 5.10 (1H, d), 7.33 (5H, s).

On the basis of the data, it is confirmed that the product is 20'-N-(O-benzylglycolyl)fortimicin B. Yield 23%.

EXAMPLE 3

Preparation of 1,6'-di-N-benzyloxycarbonyl-2'-N-[(S)-4-benzyloxycarbonylamino-2-hydroxybutyryl] fortimicin B (Compound No. 13):

In this example, 3.90 g (6.7 millimoles) of 2'-N-[(S)-4-benzyloxycarbonylamino-2-hydroxybutyryl]fortimicin B and 2 ml (14.4 millimoles) of triethylamine are dissolved in 200 ml of methanol and the solution is stirred under ice cooling (3° to 5° C.). A solution of 4.00 g (16.0 millimoles) of N-(benzyloxycarbonyloxy)- succinimide in 50 ml of tetrahydrofuran is then added dropwise to the above solution over a period of one hour. After the completion of this addition, the solution is stirred under ice cooling for one hour and at room temperature for 16 hours. The solvent is distilled off from the reaction solution and the resulting solid residue is dissolved in 250 ml of chloroform. The thus obtained solution is then washed twice with 100 ml of water and dried with anhydrous sodium sulfate. Then the chloroform solution is concentrated to dryness under reduced pressure to obtain a solid residue. The solid residue is dissolved in a small amount of chloroform and the chloroform solution is charged into a column packed with 200 g of silica gel (Kieselgel 60 made by E. Merck & Co.). Elution is carried out with a solvent system of chloroform-methanol (95:5 by volume). The eluate is taken in 16 ml fractions. Fractions Nos. 121 to 370 containing a compound having an Rf value of 0.31 in solvent system D are combined and the solvent is distilled off to obtain 3.12 g of a white solid. PMR (methanol-$d_4$) spectra of the product is as follows:

$\delta$ 1.03 (3H, d), 1.2–1.9 (6H, m), 2.37 (3H, s), 3.48 (3H, s), 5.06 (6H, s), 7.30 (15H, s)

On the basis of the data, it is confirmed that the product is 1,6'-di-N-benzyloxycarbonyl-2'-N-[(S)-4-benzyloxycarbonylamino-2-hydroxybutyryl]fortimicin B. Yield 54%.

EXAMPLE 4

Preparation of 1,6'-di-N-benzyloxycarbonyl-2'-N-(O-benzylglycolyl) fortimicin B (Compound No. 14):

In this example, 1.30 g (2.62 millimoles) of 2'-N-(O-benzylglycolyl)fortimicin B obtained in Example 2 is dissolved in 50 ml of methanol and the solution is stirred under ice cooling (3° to 5° C.). To the solution, 1.43 g (5.75 millimoles) of N-(benzyloxycarbonyloxy) succinimide is added and the solution is stirred at room temperature for 18 hours. The solvent in the reaction solution is then distilled off to obtain a solid residue. The solid residue is dissolved in 50 ml of chloroform, and the solution is washed twice with 30 ml of water and dried with anhydrous sodium sulfate. The chloroform solution is concentrated to dryness under reduced pressure to obtain a solid residue. The solid residue is dissolved in a small amount of chloroform and charged into a column packed with 60 g of silica gel as in Example 3. Elution is carried out with a solvent system of chloroform-methnol (95:5 by volume). The eluate is taken in 16 ml fractions. Fraction Nos. 14 to 66 containing a compound having an Rf value of 0.41 in solvent system D are combined and the solvent is distilled off to obtain 1.30 g of 1,6'-di-N-benzyloxycarbonyl-2'-N-(O-benzylglycolyl) fortimicin B as a white solid. Yield 65%.

EXAMPLE 5

Preparation of 2'-N-glycylfortimicin B (Compound No. 15):

In this example, 100 g of the sulfate of fortimicin A, which corresponds to 61 g (150 millimoles) of fortimicin A, is dissolved in 2 L. of water. The solution is adjusted to a pH of about 9 with potassium carbonate and then to a pH of 10 with 5N sodium hydroxide solution and heated under reflux for 4 hours. After cooling to room temperature, the reaction solution is adjusted to a pH of 7 with concentrated hydrochloric acid and passed through a column packed with 2 L. of Amberlite IRC-50 ($NH_4^+$ form). The column is washed with 10 L. of water and then elution is carried out with 0.1 N aqueous ammonia. Then, 5 L. of early eluate is collected and the successive eluate is taken in 0.5 L. fractions. Fraction Nos. 3 to 27 containing a compound having an Rf value of 0.45 in solvent system A are combined. The solvent is distilled off to obtain 37.6 g of a white solid. PMR (deuterium oxide) spectra of the product is as follows:

$\delta$ 1.07 (3H, d), 1.2–1.8 (4H, m), 2.41 (3H, s), 3.31 (2H, s), 3.50 (3H, s), 5.20 (1H, d).

On the basis of the data, it is confirmed that the product is 2'-N-glycylfortimicin B. Yield 62%

EXAMPLE 6

Preparation of 2'-N-hydantoylfortimicin B (Compound No. 16):

In this example, 2.0 g (4.5 millimoles) of fortimicin C is dissolved in 20 ml of water and the solution is heated at a temperature of 60° C. for 24 hours. After cooling to room temperature, the reaction solution is adjusted to a pH of 7 with 1N hydrochloric acid and passed through a column packed with 100 ml of Amberlite CG-50 ($NH_4^+$ form). After the column is washed with 300 ml of water, elution is carried out with 0.1 N aqueous ammonia. The eluate is taken in 20 ml fractions. Fraction Nos. 20 to 26 containing a compound having an Rf value of 0.44 in solvent system A are combined and the solvent is distilled off to obtain 658 mg of a white solid. PMR (deuterium oxide) spectra of the product is as follows:

$\delta$ 1.12 (3H, d), 1.2–1.8 (4H, m), 2.38 (3H, s), 3.47 (3H, s), 3.78 (2H, s), 5.28 (1H, d).

On the basis of the data, it is confirmed that the product is 2'-N-hydantoylfortimicin B. Yield 33%.

EXAMPLE 7

Preparation of 1,6'-di-N-benzyloxycarbonyl-2'-N-(N-benzyloxycarbonylglycyl)fortimicin B (Compound 17):

In this example, 10.1 g (25 millimoles) of 2'-N-glycylfortimicin B obtained in Example 5 and 10 ml (72 millimoles) of triethylamine are dissolved in 800 ml of methanol and the solution is stirred under ice cooling (3° to 5° C.). A solution of 22.4 g (90 millimoles) of N-(benzyloxycarbonyloxy) succinimide in 200 ml of tetrahydrofuran is then added dropwise over a period of 3 hours to the above solution. After the completion of this addition, the reaction solution is stirred under ice cooling for one hour and then at room temperature for 16 hours. The solvent in the reaction solution is distilled off and the resulting residue is dissolved in 300 ml of chloroform. The solution is then washed twice with 200 ml of water and dried with anhydrous sodium sulfate. The chloroform solution is concentrated to dryness under reduced pressure to obtain a solid residue. The solid residue is then dissolved in a small amount of chloroform and charged into a column packed with 600 g of silica gel. Elution is carried out with a solvent system of chloroformmethanol (95:5 by volume) and the eluate is taken in 150 ml fractions. Fraction Nos. 23–71 containing a compound having an Rf value of 0.43 in solvent system D are combined and the solvent is distilled off to obtain 9.0 g of a white solid. PMR (methanol-$d_4$) spectra of the product is as follows:

$\delta$ 1.03 (3H, d), 1.2–1.9 (4H, m), 2.36 (3H, s), 3.47 (3H, s), 7.36 (15H, m).

On the basis of the data, it is confirmed that the product is 1,6'-di-N-benzyloxycarbonyl-2'-N-(N-benzyloxycarbonylglycyl)fortimicin B. Yield 45%.

EXAMPLE 8

Preparation of 1,6'-di-n-benzyloxycarbonyl-2'-N-hydantoylfortimicin B (Compound No. 18):

In this example, 297 mg (0.66 millimole) of 2'-N-hydantoylfortimicin B obtained in Example 6 and 0.2 ml (1.4 millimoles) of triethylamine are dissolved in 15 ml of methanol and the solution is stirred under ice cooling (3° to 5° C.). A solution of 362 mg (1.46 millimoles) of N-(benzyloxycarbonyloxy) succinimide in 5 ml of tetrahydrofuran is then added dropwise over a period of one hour to the above solution. After the completion of the addition, the solution is stirred under ice cooling for one hour and at room temperature for 16 hours. The solvent in the reaction mixture is distilled off to obtain a solid residue and the residue is dissolved in 20 ml of chloroform. The chloroform solution is then washed with 20 ml of water and dried with anhydrous sodium sulfate. The chloroform solution is concentrated to dryness under reduced pressure to obtain a solid residue. The residue is dissolved in a small amount of chloroform and charged into a column packed with 15 g of silica gel. Elution is carried out with a solvent system of isopropanol-chloroform-28% aqueous ammonia (40:1:1 by volume) and the eluate is taken in 6 ml fractions. Fraction Nos. 13 to 35 containing a compound having an Rf value of 0.64 in solvent system B are combined and the solvent is distilled off to obtain 146 mg of a white solid. PMR (methanol-d4) spectra of the product is as follows:

δ 1.13 (3H, d), 1.2–1.9 (4H, m), 2.40 (3H, s), 3.50 (3H, s), 5.06 (4H, br), 5.33 (1H, d), 7.35 (10H, s)

On the basis of the data, it is confirmed that the product is 1,6'-di-N-benzyloxycarbonyl-2'-N-hydantoylfortimicin B. Yield 31%.

EXAMPLE 9

Preparation of 1,6'-di-N-benzyloxycarbonyl-4,2'-di-N-(N-benzyloxycarbonylglycyl)fortimicin B (Compound No. 19):

In this example, 230 mg (1.1 millimoles) of N-benzyloxycarbonylglycine and 149 mg (1.1 millimoles) of 1-hydroxybenzotriazole are dissolved in 20 ml of tetrahydrofuran and the solution is stirred under ice cooling (3° to 5° C.). To the solution, 227 mg (1.1 millimoles) of N,N'-dicyclohexylcarbodiimide is added and the solution is then stirred under ice cooling for one hour. Then, to the mixed solution there is added 808 mg (1.0 millimole) of 1,6'-di-N-benzyloxycarbonyl-2'-N-(N-benzyloxycarbonylglycyl)-fortimicin B and the solution is stirred at room temperature for 19 hours. After insoluble matters in the reaction solution are removed by filtration, the solvent in the filtrate is distilled off to obtain a solid residue and the residue is then dissolved in a small amount of chloroform. The chloroform solution is charged into a column packed with 50 g of silica gel. Elution is carried out with a solvent system of chloroform-methanol (97:3 by volume) and the eluate is taken in 16 ml fractions. Fraction Nos. 22 to 37 containing a compound having an Rf value of 0.83 in solvent system D are combined and the solvent is distilled off to obtain 910 mg of a white solid. PMR (methanol-d4) spectra of the product is as follows:

δ 1.12 (3H, d), 1.3–1.8 (4H, m), 3.05 (3H, s), 3.35 (3H, s), ~5.3 (8H, br), 7.30 (20H, s)

On the basis of the data, it is confirmed that the product is 1,6'-di-N-benzyloxycarbonyl-4,2'-di-N-(N-benzyloxycarbonylglycyl)fortimicin B. Yield 91%.

EXAMPLE 10

Preparation of 1,6'-di-N-benzyloxycarbonyl-4-N-[(S)-4-benzyloxycarbonylamino-2-hydroxybutyryl]-2'-N-(N-benzyloxycarbonylglycyl)fortimicin B (Compound No. 20):

In this example, 205 mg (0.81 millimole) of (S)-4-benzyloxycarbonylamino-2-hydroxybutyric acid and 110 mg (0.81 millimole) of 1-hydroxybenzotriazole are dissolved in 10 ml of tetrahydrofuran and the solution is stirred under ice cooling (3° to 5° C.). To the solution, 167 mg (0.81 millimole) of N,N'-dicyclohexylcarbodiimide is added and the mixed solution is stirred under ice cooling for one hour. Then, 435 mg (0.54 millimole) of 1,6'-di-N-benzyloxycarbonyl-2'-N-(N-benzyloxycarbonylglycyl)fortimicin B is added and the mixed solution is stirred at room temperature for 18 hours. After the insoluble matter in the reaction solution is removed by filtration the solvent is distilled off to obtain a solid residue. The solid residue is dissolved in a small amount of chloroform and the chloroform solution is charged into a column packed with 25 g of silica gel. Elution is then carried out with a solvent system of chloroform-methanol (97:3 by volume) and the eluate is taken in 10 ml fractions. Fraction Nos. 21–35 containing a compound having an Rf value of 0.77 in solvent system D are combined and the solvent is distilled off to obtain 344 mg of a white solid. PMR (methanol-d4) spectra of the product is as follows:

δ 1.13 (3H, d), 1.2–2.0 (6H, m), 3.07 (3H, s), 3.33 (3H, s), 5.07 (8H, s), 7.30 (20H, s)

On the basis of the data, it is confirmed that the product is 1,6'-di-N-benzyloxycarbonyl-4-N-[(S)-4-benzyloxycarbonylamino-2-hydroxybutyryl]-2'-N-(N-benzyoxycarbonylglycyl-fortimicin B. Yield 61%.

EXAMPLE 11

Preparation of 1,6'-di-N-benzyloxycarbonyl-4,2'-di-N-[(S)-4-benzyloxycarbonylamino-2-hydroxybutyryl]fortimicin B (Compound No. 21):

In this example, 1.01 g (4.0 millimoles) of (S)-4-benzyloxycarbonylamino-2-hydroxybutyric acid and 0.54 g (4.0 millimoles) of 1-hydroxybenzotriazole are dissolved in 80 ml of tetrahydrofuran and the solution is stirred under ice cooling (3° to 5° C.). Then 0.83 g (4.0 millimoles) of N,N'-dicyclohexylcarbodiimide is added and the mixed solution is stirred under ice cooling for one hour. To the solution, 3.10 g (3.6 millimoles) of 1,6-di-N-benzyloxycarbonyl-2'-N-[(S)-4-benzyloxycarbonylamino-2-hydroxybutyryl]fortimicin B is added and the mixed solution is stirred at room temperature for 18 hours. After insoluble matters in the reaction mixture are removed by filtration, the solvent in the filtrate is distilled off to obtain a solid residue. The residue is dissolved in a small amount of chloroform and the chloroform solution is charged into a column packed with 100 g of silica gel. Elution is carried out with a solvent system of chloroform-methanol (95:5 by volume). The eluate is taken in 16 ml fractions. Fraction Nos. 24–66 containing a compound having an Rf value of 0.53 in solvent system D are combined and the solvent is distilled off to obtain 1.11 g of a white solid. PMR (methanol-d4) spectra of the product is as follows:

δ 1.13 (3H, d), 1.2–1.9 (8H, m), 3.10 (3H, s), 3.35 (3H, s), 7.33 (20H, s)

On the basis of the data, it is confirmed that the product is 1,6'-di-N-benzyloxycarbonyl-4,2'-di-N-[(S)-4-benzyloxycarbonylamino-2-hydroxybutyryl]fortimicin B. Yield 28%.

EXAMPLE 12

Preparation of 1,6'-di-N-benzyloxycarbonyl-4-N-[(S)-4-benzyloxycarbonylamino-2-hydroxybutyryl]-2'-N-(O-benzylglycolyl)fortimicin B (Compound No. 22):

In this example, 500 mg (1.98 millimoles) of (S)-4-benzyloxycarbonylamino-2-hydroxybutyric acid and 300 mg (1.98 millimoles) of 1-hydroxybenzotriazole are dissolved in 15 ml of tetrahydrofuran and the solution is stirred under ice cooling (3° to 5° C.). To the solution, 400 mg (1.98 millimoles) of N,N'-dicyclohexylcarbodiimide is added and the mixed solution is stirred under ice cooling for one hour. Then, 1.25 g (1.64 millimoles) of 1,6'-di-N-benzyloxycarbonyl-2'-N-(O-benzylglycolyl)-fortimicin B obtained in Example 4 is added and the mixed solution is stirred at room temperature for 46 hours. After the insoluble matters in the reaction solution are removed by filtration, the solvent is distilled off to obtain a solid residue. The residue is dissolved in a small amount of chloroform and the chloroform solution is charged into a column packed with 60 g of silica gel. Elution is carried out with a solvent system of chloroform-methanol (97:3 by volume) and the eluate is taken in 16 ml fractions. Fractions Nos. 43–54 containing a compound having an Rf value of 0.79 in solvent system E are combined and concentrated to dryness to obtain 350 mg of 1,6'-di-N-benzyloxycarbonyl-4-N-[(S)-4-benzyloxycarbonylamino-2-hydroxybutyryl]-2'-N-(O-benzylglycolyl)fortimicin B as a white solid. Yield 21%.

EXAMPLE 13

Preparation of 1,6'-di-N-benzyloxycarbonyl-4,2'-di-N-hydantoylfortimicin B:

In this example, 71 mg (0.60 millimole) of hydantoic acid and 81 mg (0.60 millimole) of 1-hydroxybenzotriazole are dissolved in 10 ml of dimethylformamide and the solution is stirred under ice cooling (3° to 5° C.). To the solution, 124 mg (0.60 millimole) of N,N'-dicyclohexylcarbodiimide is added and the mixed solution is stirred under ice cooling for one hour. Then, 330 mg (0.46 millimole) of 1,6'-di-N-benzyloxycarbonyl-2'-N-hydantoylfortimicin B obtained as in Example 8 is added and the mixed solution is stirred at room temperature for 41 hours. After insoluble matters in the reaction solution are removed by filtration, the solvent in the filtrate is distilled off to obtain a solid residue containing 1,6'-di-N-benzyloxycarbonyl-4,2'-di-N-hydantoylfortimicin B.

EXAMPLE 14

Preparation of 2'-N-glycylfortimicin A (Compound No. 23):

In this example, 500 mg (0.50 millimole) of 1,6'-di-N-benzyloxycarbonyl-4,2'-di-N-(N-benzyloxycarbonylglycyl) fortimicin B obtained in Example 9 is dissolved in 24 ml of 0.2N hydrochloric acid-methanol solution wherein 12N hydrochloric acid is diluted with methanol to make the solution 0.2N (the same as below). To the solution, about 50 mg of 10% palladium-carbon is added and then hydrogen gas is bubbled at room temperature and atmospheric pressure. After the catalyst in the reaction mixture is removed by filtration, the filtrate is concentrated to dryness under reduced pressure to obtain a residue. The residue is dissolved in about 5 ml of water and the solution is then adjusted to a pH of 7. The solution is passed through a column packed with 20 ml of Amberlite CG-50 (NH$_4$+ form). After the column is washed with 100 ml of water, elution is carried out with 0.3N aqueous ammonia and the eluate is taken in 5 ml fractions. Fraction Nos. 12 to 14 containing a compound having an Rf value of 0.42 in solvent system A are combined and the solvent is distilled off to obtain 97 mg of a white solid. Properties of the product are as follows:

Mass spectra: m/e 463 (M$^+$+1), 462 (M$^+$), 445, 416, 328, 246, 207, 200

PMR (deuterium oxide): δ 1.13 (3H, d), 1.3–1.9 (4H, m), 3.05 (3H, s), 3.44 (3H, s), 4.65 (1H, d-d), 4.95 (1H, d)

On the basis of the data, it is confirmed that the product is 2'-N-glycylfortimicin A. Yield 42%.

EXAMPLE 15

Preparation of 4-N-[(S)-4-amino-2-hydroxybutyryl]-2'-N-glycylfortimicin B (Compound No. 24):

In this example, 4.03 g (3.86 millimoles) of 1,6'-di-N-benzyloxycarbonyl-4-N-[(S)-4-benzyloxycarbonylamino-2-hydroxybutyryl]-2'-N-(N-benzyloxycarbonylglycyl)fortimicin B obtained as in Example 10 is dissolved in 150 ml of methanol solution containing 2.3 ml (31 millimoles) of trifluoroacetic acid. To the solution, about 200 mg of 10% palladium-carbon is added and hydrogen gas is bubbled at room temerature and atmospheric pressure. After the catalyst in the reaction mixture is removed by filtration, the filtrate is concentrated to dryness to obtain 3.84 g of the trifluoroacetate of 4-N-[(S)-4-amino-2-hydroxybutyryl]-2'-N-glycylfortimicin B as a grayish white solid. The Rf value of the product on TLC in solvent system A is 0.28.

EXAMPLE 16

Preparation of 2'-N-hydantoylfortimicin C (Compound No. 4):

In this example, all of the 1,6'-di-N-benzyloxycarbonyl-4,2'-di-N-hydantoylfortimicin B obtained in Example 13 is dissolved in 15 ml of 0.2N hydrochloric acid-methanol solution and about 30 mg of 10% palladium-carbon is then added thereto. Hydrogen gas at room temperature and atmospheric pressure is then bubbled therethrough. The catalyst in the reaction mixture is removed by filtration, and the filtrate is concentrated to dryness under reduced pressure to obtain a residue. The residue is dissolved in about 2 ml of water. The solution is then adjusted to a pH of 7 with 1N sodium hydroxide and passed through a column packed with 10 ml of Amberlite CG-50 (NH$_4$+ form). After the column is washed with 50 ml of water, elution is carried out with 0.03N aqueous ammonia and the eluate is taken in 2 ml fractions. Fraction Nos. 33 to 51 containing a compound having an Rf value of 0.31 in solvent system A are combined and the solvent is distilled off to obtain 104 mg of a white solid. PMR (deuterium oxide) spectra of the product is as follows:

δ 1.04 (3H, d), 1.2–1.9 (4H, m), 3.10 (3H, s), 3.44 (3H, s), 4.87 (1H, d), 4.95 (1H, d-d).

On the basis of the data, it is confirmed that the product is 2'-N-hydantoylfortimicin C. Yield 41%.

Then 110 mg (0.2 millimole) of the thus obtained 2'-N-hydantoylfortimicin C is dissolved in 2 ml of water and the solution is adjusted to a pH of 4 with 5N sulfuric acid. The solution is then added dropwise to 30 ml of ethanol and the resulting precipitate is collected and dried to obtain 124 mg (0.18 millimole) of the sulfate of the compond as a white powder. Yield 87%.

$[\alpha]_D^{23°} = +58.5°$ (c=0.2, water)

Elementary analysis

Calculated as $C_{21}H_{40}N_8O_9 \cdot H_2SO_4 \cdot C_2H_5OH \cdot H_2O$ C, 38.86%: H, 7.09%: N, 15.77%;

Found: C, 38.76%: H, 6.95%: N, 16.03%.

EXAMPLE 17

Preparation of 4,2'-di-N-[(S)-4-amino-2-hydroxybutyryl]fortimicin B (Compound No. 25):

In this example, 1.07 g (0.99 millimole) of 1,6'-di-N-benzyloxycarbonyl-4,2'di-N-[(S)-4-benzyloxycarbonylamino-2-hydroxybutyryl]fortimicin B obtained in Example 11 is dissolved in 60 ml of methanol containing 0.6 ml (8.1 millimoles) of trifluoroacetic acid and about 100 mg of 10% palladium-carbon is then added to the solution. Through the reaction mixture hydrogen gas is bubbled at room temperature and atmospheric pressure. After the catalyst in the reaction mixture is removed by filtration, the filtrate is concentrated to dryness to obtain 1.06 g of the trifluoroacetate of 4,2'-di-N-[(S)-4-amino-2-hydroxybutyryl]-fortimicin B as a grayish white solid. The product shows an Rf value of 0.13 on TLC in solvent system A.

EXAMPLE 18

Preparation of 4-N-[(S)-4-amino-2-hydroxybutyryl]-2'-N-glycolylfortimicin B (Compound No. 26):

In this example, 780 mg (0.78 millimole) of 1,6'-di-N-benzyloxycarbonyl-4-N-[(S)-4-benzyloxycarbonylamino-2-hydroxybutyryl]-2'-N-(O-benzylglycolyl)fortimicin B obtained as in Example 12 is dissolved in 20 ml of methanol containing 0.40 g (3.5 millimoles) of trifluoroacetic acid and about 50 mg of 10% palladium-carbon is added to the solution. Through the reaction mixture hydrogen gas is bubbled at room temperature and atmospheric pressure. After the catalyst in the reaction mixture is removed by filtration, the filtrate is concentrated to dryness to obtain the trifluoroacetate of 4-N-[(S)-4-amino-2-hydroxybutyryl]-2'-N-glycolylfortimicin B as a grayish white solid. The product shows an Rf value of 0.32 on TLC in solvent system C.

EXAMPLE 19

Preparation of 4,2'-di-N-(2-aminoethyl)fortimicin B (Compound No. 5):

In this example, 170 mg (0.37 millimole) of 2'-N-glycylfortimicin A obtained as in Example 14 is suspended in 10 ml of tetrahydrofuran and 5 ml (5 millimoles) of 1M diborane-tetrahydrofuran solution is added thereto. The reaction mixture is heated by reflux with stirring for one hour. After the reaction mixture is cooled to room temperature, 0.5 ml of water is added thereto to decompose excess diborane and the resulting solution is then concentrated to dryness under reduced pressure. To the resulting residue 10 ml of 80% aqueous hydrazine is added and the mixture is heated by reflux for 3 hours and then concentrated to dryness. The thus obtained residue is dissolved in about 10 ml of water and the solution is adjusted to a pH of 6 with 1 N hydrochloric acid. The solution is then passed through a column packed with 10 ml of Amberlite CG-50 ($NH_4^+$ form). After the column is washed with 50 ml of water, elution is carried out with 0.6N aqueous ammonia and the eluate is taken in 5 ml fractions. Fraction Nos. 22 to 46 containing a compound having an Rf value of 0.35 in solvent system A are combined and the solvent is distilled off to obtain 139 mg of a white solid. Properties of the product are as follows:

Mass spectra: m/e 435 (M+), 417, 404, 387, 375, 367, 361, 344, 325, 301, 278, 262, 250, 233, 219, 207, 198, 186, 169, 155, 142, 129

PMR (deuterium oxide): δ 1.06 (3H, d), 1.2–1.9 (4H, m), 3.43 (3H, s), 5.10 (1H, d)

On the basis of the data, it is confirmed that the product is 4,2'-di-N-(2-aminoethyl)fortimicin B. Yield 85%.

Then, 110 mg (0.25 millimole) of 4,2'-di-N-(2-aminoethyl)fortimicin B obtained above is dissolved in 2 ml of water and the solution is adjusted to a pH of 4 with 5N sulfuric acid. The solution is then added dropwise to 20 ml of ethanol and the resulting precipitate is collected. The precipitate is dried to obtain 180 mg (0.23 millimole) of the sulfate of the compound as a white powder. Yield 92%. Properties of the product are as follows:

$[\alpha]_D^{23°} = +61.0°$ (c=0.5, water)

Elementary analysis

Calculated as $C_{19}H_{42}N_6O_5 \cdot 3H_2SO_4 \cdot C_2H_5OH \cdot 2H_2O$
C, 31.10%: H, 7.21%: N, 10.36%
Found C, 31.01%: H, 7.50%: N, 10.40%

EXAMPLE 20

Preparation of 4-N-[(S)-4-amino-2-hydroxybutyl]-2'-N-glycylfortimicin B (Compound No. 6) and 4-N-[(S)-4-amino-2-hydroxybutyl]-2'-N-(2-aminomethyl)fortimicin B (Compound No. 7):

In this example, 50 ml of 1M diborane-tetrahydrofuran solution is added to 3.46 g (3.5 millimoles) of the trifluoroacetate of 4-N-[(S)-4-amino-2-hydroxybutyrl]-2'-N-glycylfortimicin B obtained in Example 15 and the mixture is stirred at room temperature for 30 minutes. After about 10 ml of water is added to the reaction mixture under ice cooling to decompose excess diborane, the solvent is distilled off to obtain a solid residue. To the residue 150 ml of 0.2N hydrochloric acid-methanol solution is added and the mixture is heated at temperature of 50° C. for 4 hours. The solvent in the mixture is distilled off to obtain a solid residue. The residue is dissolved in about 50 ml of water and the solution is adjusted to a pH of 7 with 1N sodium hydroxide. The solution is passed through a column packed with 100 ml of Amberlite CG-50 ($NH_4^+$ form). After the column is washed with about 500 ml of water, elution is carried out with 0.4N aqueous ammonia and the eluate is taken in 20 ml fractions. Fraction Nos. 13 to 26 containing a compound having an Rf value of 0.33 in solvent system A are combined and the solvent is distilled off to obtain 494 mg of a white solid. Properties of the product are as follows:

Mass spectra: m/e 493 (M++1), 492 (M+), 474, 444, 418, 387, 322, 294, 245, 219, 200

PMR (deuterium oxide): δ1.06 (3H, d), 1.2–1.9 (6H, m), 2.40 (3H, s), 3.29 (2H, s), 3.43 (3H, s), 5.10 (1H, d)

On the basis of the data, it is confirmed that the product is 4-N-[(S)-4-amino-2-hydroxybutyl]-2'-N-glycylfortimicin B. Yield 29%. The sulfate of the compound is prepared as in Example 19.

$[\alpha]_D^{23°} = +70.0°$ (c=0.2, water)

Elementary analysis

Calculated as $C_{21}H_{44}N_6O_7 \cdot 2.5H_2SO_4 \cdot C_2H_5OH \cdot H_2O$
C, 34.45%: H, 7.17%: N, 10.48%
Found C, 34.29%: H, 7.45%: N, 10.61%

Then, elution is carried out with 0.5N aqueous ammonia and the eluate is taken in 20 ml fractions. Fraction Nos. 11 to 90 containing a compound having an Rf value of 0.30 in solvent system A are combined and the solvent is distilled off to obtain 638 mg of a white powder. Properties of the product are as follows:

Mass spectra: m/e 479 (M$^+$+1), 478 (M$^+$), 460, 448, 443, 430, 404, 375, 373, 361, 344, 338, 322, 311, 306, 294, 272, 245, 219, 207, 202, 186, 173, 169, 155, 142, 126

PMR (deuterium oxide): δ1.04 (3H, d), 1.2–1.9 (4H, m), 2.43 (3H, s), 3.43 (3H, s), 5.13 (1H, d)

On the basis of the data, it is confirmed that the product is 4-N-[(S)-4-amino-2-hydroxybutyl]-2'-N-(2-aminoethyl) fortimicin B. Yield 38%.

The sulfate of the compound is prepared as in Example 19.

$[\alpha]_D^{23°} = +67.0°(c=0.2$, water)

Elementary analysis

Calculated as $C_{21}H_{46}N_6O_6 \cdot 3H_2SO_4 \cdot C_2H_5OH \cdot H_2O$ C, 33.00%: H, 7.23%: N, 9.98%

Found C, 32.76%: H, 7.18%: N, 9.70%

EXAMPLE 21

Preparation of 4-N-[(S)-4-amino-2-hydroxybutyl]-2'-N-[(S)-4-amino-2-hydroxybutyryl]fortimicin B (Compound No. 8) and 4,2'-di-N-[(S)-4-amino-2-hydroxybutyl]fortimicin B (Compound No. 9):

In this example, 1.06 g (0.99 millimole) of the trifluoroacetate of 4,2'-di-N-[(S)-4-amino-2-hydroxybutyryl]-fortimicin B obtained in Example 17 is dissolved in 30 ml of tetrahydrofuran. To the solution, 15 ml of 1M diborane-tetrahydrofuran is added and the mixture is stirred at room temperature for 30 minutes. After about 5 ml of water is added to the reaction mixture under ice cooling to decompose excess diborane, the solvent is distilled off to obtain a residue. To the residue 50 ml of 0.2N hydrochloric acid-methanol solution is added. The solution is heated at a temperature of 50° C. for 4 hours and the solvent is distilled off to obtain a residue. The residue is dissolved in about 20 ml of water. The solution is then adjusted to a pH of 7 with 1N sodium hydroxide and passed through a column packed with 25 ml of Amberlite CG-50 (NH$_4$+form). After the column is washed with 150 ml of water and 180 ml of aqueous ammonia, elution is carried out with 0.5N aqueous ammonia. The eluate is taken in 10 ml fractions. Fraction Nos. 6 to 100 containing a compound having an Rf value of 0.25 in solvent system A are combined and the residue is concentrated to dryness to obtain 86 mg of a white solid. Properties of the product are as follows:

Mass spectra: m/e 537 (M$^+$+1), 387, 361, 344, 322, 294, 226, 219, 143

PMR (deuterium oxide): δ1.05 (3H, d), 1.2–1.9 (8H, m), 2.43 (3H, s), 3.43 (3H, s), 5.07 (1H, d)

On the basis of the data, it is confirmed that the product is 4-N-[(S)-4-amino-2-hydroxybutyl]-2'-N-[(S)-4-amino-2-hydroxybutyryl]fortimicin B. Yield 16%.

The sulfate of the compound is prepared as in Example 19.

$[\alpha]_D^{25°} = +87.5°(c=0.2$, water)

Elementary analysis

Calculated as $C_{23}H_{48}N_6O_8 \cdot 2.5H_2SO_4 \cdot C_2H_5OH \cdot 1.5H_2O$ C, 34.76%: H, 7.35%: N, 9.73%

Found C, 34.84%: H, 7.61%: N, 9.78%

Then, elution is carried out with 0.6N aqueous ammonia and the eluate is taken in 10 ml fractions. Fraction Nos. 82–170 containing a compound having an Rf value of 0.20 in solvent system A are combined and the solvent is distilled off to obtain 150 mg of a white solid. Properties of the product are as follows:

Mass spectra: m/e 523 (M$^+$+1), 487, 474, 448, 401, 344, 322, 294, 230, 219, 213, 207, 175, 155

PMR (deuterium oxide): δ1.05 (3H, d), 1.2–1.9 (8H, m), 2.44 (3H, s), 3.43 (3H, s), 5.20 (1H, d)

On the basis of the data, it is confirmed that the product is 4,2'-di-N-[(S)-4-amino-2-hydroxybutyl]fortimicin B.

The sulfate of the compound is prepared as in Example 19.

$[\alpha]_D^{23°} = +88.0°(c=0.2$, water)

Elementary analysis

Calculated as $C_{23}H_{50}N_6O_7 \cdot 3H_2SO_4 \cdot 1.5H_2O$ C, 33.74%: H, 7.36%: N, 9.44%

Found C, 33.77%: H, 7.61%: N, 9.20%

EXAMPLE 22.

Preparation of 4-N-[(S)-4-amino-2-hydroxybutyl]-2'-N-(2-hydroxyethyl)fortimicin B (Compound No. 10):

In this example, 15 ml of 1M diborane-tetrahydrofuran solution is added to all of the trifluoroacetate of 4-N-[(S)-4-amino-2-hydroxybutyryl]-2'-N-glycolylfortimicin B obtained in Example 18 and the mixture is heated by reflux with stirring for 2 hours. After the reaction solution is cooled to room temperature, about 2 ml of water is added thereto to decompose excess diborane and the solvent is distilled off. To the resulting residue, 20 ml of 0.2N hydrochloric acid-methanol solution is added and the solution is allowed to stand at room temperature for 23 hours. Then, the solvent is distilled off. The resulting residue is dissolved in about 10 ml of water. The solution is adjusted to a pH of 7 and passed through a column packed with 30 ml of Amberlite CG-50 (NH$_4$+form). After the column is washed with 150 ml of water and 300 ml of 0.2N aqueous ammonia, elution is carried out with 0.4N aqueous ammonia. The eluate is taken in 20 ml fractions. Fraction Nos. 14 to 21 containing a compound having an Rf value of 0.50 in solvent sysem C are combined and the solvent is distilled off to obtain 228 mg of a white solid. Properties of the product are as follows:

Mass spectra: m/e 480 (M$^+$+1), 444, 431, 405, 322, 294, 261, 219, 203, 187

PMR (deuterium oxide): δ1.02 (3H, d), 1.2–1.9 (6H, m), 2.40 (3H, s), 3.42 (3H, s), 5.15 (1H, d)

On the basis of the data, it is confirmed that the product is 4-N-[(S)-4-amino-2-hydroxybutyl]-2'-N-(2-hydroxyethyl) fortimicin B. Yield 61%.

The sulfate of the compound is prepared as in Example 19. Properties of the product are as follows:

$[\alpha]_D^{23°} = +59.5°(c=0.2$, water)

Elementary analysis

Calculated as $C_{21}H_{45}N_5O_7 \cdot 2.5H_2SO_4 \cdot C_2H_5OH \cdot H_2O$ C, 35.01%: H, 7.41%: N, 8.89%

Found C, 34.92%: H, 7.56%: N, 8.67%

EXAMPLE 23

Peparation of 1,6'-di-N-benzyloxycarbonyl-4-N-[(S)-4-benzyloxycarbonylamino-2-hydroxybutyl]-2'-N-(N-benzyloxycarbonylglycyl)fortimicin B (Compound No. 27) and 1,6'-di-N-benzyloxycarbonyl-4-N-[(S)-4-benzyloxycarbonylamino-2-hydroxybutyl]-2'-N-(2-benzyloxycarbonylaminoethyl)fortimicin B (Compound No. 28):

In this example, 324 mg (0.30 millimole) of 1,6'-di-N-benzyloxycarbonyl-4-N-[(S)-4-benzyloxycarbonylamino-2-hydroxybutyryl]-2'-N-(N-benzyloxycarbonylglycyl)fortimicin B obtained in Example 10 is dissolved in 10 ml of tetrahydrofuran. To the solution 5 ml of 1M diborane-tetrahydrofuran solution is added and the mixture is stirred at room temperature for 5 minutes. About 1 ml of water is added to the reaction mixture to decompose excess diborane and the solvent is distilled off. To the resulting solid residue 24 ml of 0.2N hydrochloric acid-methanol solution is added. The solution is allowed to stand at room temperature for 46 hours and the solvent is then distilled off. To the resulting solid residue 20 ml each of chloroform and 5% sodium bicarbonate is added and the mixture well stirred is then subjected to separation. The water layer is washed twice with 10 ml of chloroform. After the chloroform layer and the washed chloroform are combined and washed with 10 ml of water, the combined chloroform solution is dried with anhydrous sodium sulfite. The chloroform solution is concentrated to dryness to obtain a residue. The residue is dissolved in a small amount of chloroform and passed through a column packed with 15 g of silica gel. Elution is carried out with a solvent system of chloroform-methanol (96:4 by volume) and the eluate is taken in 7 ml fractions. Fractions Nos. 21-26 containing a compound having an Rf value of 0.51 in solvent system D are combined and the solvent is distilled off to obtain 51 mg of a white solid. PMR (methanol-$d_4$) spectra of the product is as follows:

$\delta$1.03 (3H, d), 1.2-1.9 (6H, m), 2.46 (3H, s), 3.40 (3H, s), 7.30 (20H, s)

On the basis of the data, it is confirmed that the product is 1,6'-di-N-benzyloxycarbonyl-4-N-[(S)-4-benzyloxy-carbonylamino-2-hydroxybutyl]-2'-N-(N-benzyloxycarbonylglycyl)fortimicin B. Yield 16%.

Fraction Nos. 36 to 66 containing a compound having an Rf value of 0.15 in solvent system D are combined and the solvent is distilled off to obtain 121 mg of a white solid. PMR (methanol-$d_4$) spectra of the product is as follows:

$\delta$1.02 (3H, d), 1.2-1.9 (6H, m), 2.40 (3H, s), 3.39 (3H, s), 7.33 (20H, s)

On the basis of the data, it is confirmed that the product is 1,6'-di-N-benzyloxycarbonyl-4-N-[(S)-4-benzyloxycarbonylamino-2-hydroxybutyl]-2'-N-(2-benzyloxycarbonylaminoethyl)fortimicin B. Yield 38%.

EXAMPLE 24

Preparation of 4-N-[(S)-4-amino-2-hydroxybutyl]-2'-N-glycylfortimicin B (Compound No. 6):

In this example, 51 mg of 1,6'-di-N-benzyloxycarbonyl4-N-[(S)-4-benzyloxycarbonylamino-2-hydroxybutyl]-2'-N-(N-benzyloxycarbonylglycyl)fortimicin B obtained in Example 23 is dissolved in 10 ml of 0.2N hydrochloric acid-methanol solution. About 5 mg of 10% palladium-carbon is added to the solution and then hydrogen gas at room temperature and atmospheric pressure is bubbled therethrough. The catalyst is the reaction mixture is removed by filtration and the filtrate is concentrated to dryness to obtain a residue. The residue is then dissolved in about 2 ml of water. The solution is adjusted to a pH of 7 with 1N sodium hydroxide and passed through a column packed with 5 ml of Amberlite CG-50 ($NH_4$ $^{30}$ form). After the column is washed with about 25 ml of water, elution is carried out with 0.6N aqueous ammonia and the eluate is taken in 2 ml fractions. Fraction Nos. 11 to 16 containing a compound having an Rf value of 0.33 in solvent system A are combined and the solvent is distilled off to obtain 16 mg of a white solid. Since the product is coincident with the compound obtained in Example 20 in Rf values on TLC and mass spectrum, it is confirmed that the product is 4-N-[(S)-4-amino-2-hydroxybutyl]-2'-N-glycylfortimicin B. Yield 40%.

EXAMPLE 25

Preparation of 4-N-[(S)-4-amino-2-hydroxybutyl]-2'-N-(2-aminoethyl)-fortimicin B (Compound No. 7):

In this example, 121 mg (0.12 millimole) of 1,6'-di-N-benzyloxycarbonyl-4-N-[(S)-4-benzyloxycarbonylamino-2-hydroxybutyl]-2'-N-(2-benzyloxycarbonylaminoethyl)fortimicin B obtained in Example 23 is dissolved in 15 ml of 0.2N hydrochloric acid-methanol solution. To the solution about 10 mg of 10% palladium-carbon is added and then hydrogen gas at room temperature and atmospheric pressure is bubbled therethrough. After the catalyst in the reaction mixture is removed by filtration, the filtrate is concentrated to dryness under reduced pressure to obtain a residue. The residue is dissolved in about 2 ml of water. The soluton is adjusted to a pH of 7 with 1N sodium hydroxide and passed through a column packed with 5 ml of Amberlite CG-50 ($Nh_4^+$ form). After the column is washed with about 25 ml of water, elution is carried out with 0.6N aqueous ammonia and the eluate is taken in 2.5 ml fractions. Fraction Nos. 20 to 40 containing a compound having an Rf value of 0.30 in solvent system A are combined and the solvent is distilled off to obtain 27 mg of a white solid. Since the product is coincident with the compound obtained in Example 20 in the Rf values on TLC and mass spectrum, it is confirmed that the product is 4-N-[(S)-4-amino-2-hydroxybutyl]-2'-N-(2-aminoethyl)fortimicin B. Yield 47%.

What is claimed is:

1. 4,2'-di-N-substituted derivatives of fortimicin B, represented by the formula:

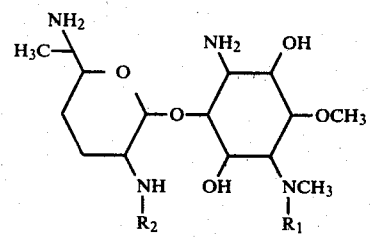

wherein $R_1$ represents a

or -$CH_2$-$R_3$ group, and $R_2$ represents a

or —$CH_2$—$R_4$ group and wherein $R_4$ represents an aminoalkyl group having 1 to 8 carbon atoms, hydroxyalkyl group having 1 to 8 carbon atoms, carbamoylaminoalkyl group having 2 to 9 carbon atoms or $\omega$-aminohydroxyalkyl group having 2 to 9 carbon atoms wherein the amino group and hydroxy group are bonded to different carbon atoms, and $R_3$ represents a carbamoylaminoalkyl group having 2 to 9 carbon atoms, and the pharmaceutically acceptable non-toxic acid addition salts thereof.

2. 4,2'-di-N-substituted derivatives of fortimicin B according to claim 1, wherein the derivatives are represented by the formula:

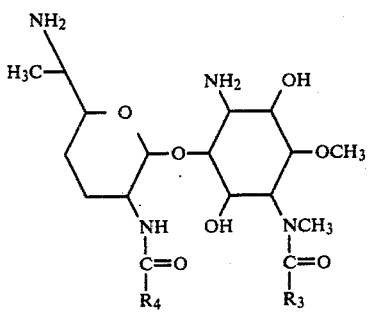

wherein $R_3$ and $R_4$ have the same significance as defined in claim 1 and the pharmaceutically acceptable non-toxic acid addition salts thereof.

3. 4,2'-di-N-substituted derivatives of fortimicin B according to claim 1, wherein the derivatives are represented by the formula:

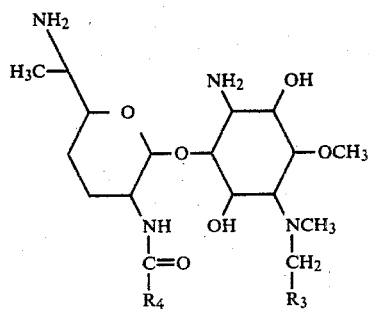

wherein $R_3$ and $R_4$ have the same significance as defined in claim 1 and the pharmaceutically acceptable non-toxic acid addition salts thereof.

4. 4,2'-di-N-substituted derivatives of fortimicin B according to claim 1, wherein the derivatives are represented by the formula:

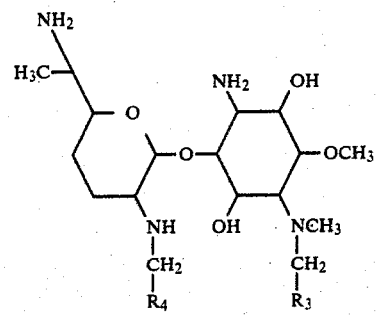

wherein $R_3$ and $R_4$ have the same significance as defined in claim 1 and the pharmaceutically acceptable non-toxic acid addition salts thereof.

5. 4,2'-di-N-substituted derivatives of fortimicin B according to claim 1, wherein the derivatives are represented by the formula:

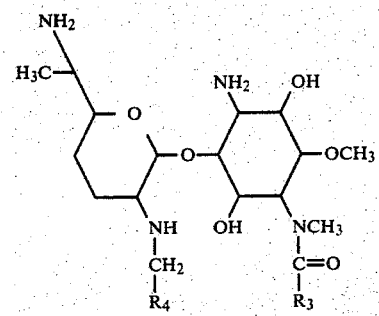

wherein $R_3$ and $R_4$ have the same significance as defined in claim 1 and the pharmaceutically acceptable non-toxic acid addition salts thereof.

* * * * *